(12) United States Patent
Zandonà et al.

(10) Patent No.: US 9,918,741 B2
(45) Date of Patent: Mar. 20, 2018

(54) ANCHORING GROUP FOR EXTERNAL FIXATOR

(71) Applicant: Orthofix S.r.l., Bussolengo (Verona) (IT)

(72) Inventors: Enrico Zandonà, Quinto di Valpantena (IT); Andrea Ottoboni, Rovigo (IT); Daniele Venturini, Povegliano Veronese (IT); Michele Coati, San Pietro In Cariano (IT)

(73) Assignee: Orthofiz S.R.L., Verona (IT)

( * ) Notice: Subject to any disclaimer, the term of this patent is extended or adjusted under 35 U.S.C. 154(b) by 155 days.

(21) Appl. No.: 14/104,922

(22) Filed: Dec. 12, 2013

(65) Prior Publication Data

US 2015/0038966 A1 Feb. 5, 2015

(30) Foreign Application Priority Data

Jul. 31, 2013 (EP) ..................................... 13178834

(51) Int. Cl.
*A61B 17/64* (2006.01)
*A61B 17/56* (2006.01)

(52) U.S. Cl.
CPC .......... *A61B 17/6466* (2013.01); *A61B 17/64* (2013.01); *A61B 2017/564* (2013.01)

(58) Field of Classification Search
USPC ..................................... 606/54, 59
See application file for complete search history.

(56) References Cited

U.S. PATENT DOCUMENTS

| 5,003,969 A | * | 4/1991 | Azer | ..................... A61F 5/0585 606/54 |
| 6,221,072 B1 | | 4/2001 | Termaten | |
| 2004/0260291 A1 | * | 12/2004 | Jensen | ............... A61B 17/1655 606/915 |

(Continued)

FOREIGN PATENT DOCUMENTS

| WO | 95/10240 A1 | 4/1995 | |
| WO | WO 95/10240 | * 4/1995 | ............. A61B 17/60 |
| WO | 2014/111907 A1 | 7/2014 | |

OTHER PUBLICATIONS

International Search Report and Written Opinion, PCT/EP2014/001893, dated Oct. 20, 2014, 8 pages.

*Primary Examiner* — Nicholas Plionis

(57) ABSTRACT

The present disclosure relates to an anchoring group for an external fixator, that comprises a connecting body designed to be coupled to a bar of an external fixator. A locking device is connected to the connecting body at a fastening point thereof and comprises a pin locking arm provided with two seats suitable for locking a corresponding number of uni-cortical pins. A connection base is intended to be coupled to a connecting body of the anchoring group. An additional member, also associated with the connecting body, comprises at least one auxiliary seat, not aligned with the seats of the locking device, for locking an additional uni-cortical pin. In an additional embodiment, the connection base of the locking device extends in an angled relationship with respect to the pin locking arm and away from both the seats. The connection base has a point for fastening to the connecting body which is not aligned with said seats.

10 Claims, 18 Drawing Sheets

(56) References Cited

U.S. PATENT DOCUMENTS

| | | | |
|---|---|---|---|
| 2008/0275552 A1* | 11/2008 | Makower | A61B 17/68 623/13.13 |
| 2010/0318084 A1* | 12/2010 | Hajianpour | A61B 17/62 606/59 |
| 2011/0009865 A1* | 1/2011 | Orfaly | A61B 17/1717 606/62 |
| 2014/0025076 A1* | 1/2014 | Lee, Jr. | A61B 17/6466 606/59 |
| 2014/0257288 A1* | 9/2014 | Chang | A61B 17/6466 606/59 |
| 2016/0022315 A1 | 1/2016 | Soffiatti et al. | |

* cited by examiner

ANCHORING GROUP FOR EXTERNAL FIXATOR

CROSS-REFERENCE TO RELATED APPLICATION(S)

This application claims priority to European Patent Application 13178834.1 which was filed Jul. 31, 2013 and is incorporated herein by reference in its entirety.

TECHNICAL FIELD

The present disclosure pertains to the field of orthopaedic surgery and relates in particular to the application of an external fixator to a long bone by means of unicortical pins.

The disclosure also relates to an anchoring group comprising the aforementioned pin-locking device articulated to a locking clamp of an external fixator bar, as well as to an external fixator comprising said anchoring group.

BACKGROUND

External fixators are widely used for the treatment of bone fractures or for joining together two or more bone fragments. Known fixators comprise bone screws which are inserted in the bones and use external devices such as fixation clamps, fixation bars, rings, etc., that allow the creation of a rigid structure able to hold together the bone fragments in the desired position until completely healed.

These external fixators have the advantage of ensuring strength and stability owing, among other things, to the use of bone screws which penetrate into the bones at a sufficient depth; in particular, these screws pass through the bone cortex in two points so as to provide a flexurally resistant fastening.

However, the use of bi-cortical screws may be excessively invasive for patients in critical conditions, who for example have multiple fractures along with, in some case, extensive wounds and/or contusions. In particular the time devoted to checking the tip which emerges from the second cortex may be critical.

Also, with particular reference to the reduction of fractures in long bones, the aforementioned bi-cortical screws pass through the medullary cavity, which makes it impossible to simultaneously insert a medullary nail, which is particularly suitable for the treatment of certain types of trauma.

Moreover, the surgical implant of a definitive fixator of the aforementioned type requires time and suitable facilities and is not always compatible with the unforeseen circumstances where rapid intervention is required; for example, it is relatively difficult to perform the implant of such an external fixator in the context of a field hospital or in any case under environmental conditions where sterility is not guaranteed and where the fracture must be treated as a matter of emergency.

In order to meet these specific needs, external fixators of a provisional nature have been developed that, in addition to having a structure which is generally slimmer and lighter, use unicortical screws or unicortical pins for the attachment to the bone, i.e. that have been designed to be screwed in superficially so that they are attached to a single bone cortex only.

The unicortical pin undoubtedly represents a less invasive fixation system than conventional bone screws; moreover, owing to its limited penetration, the pin does not reach the medullary cavity of the bone, thus avoiding the risk of unwanted infections.

On the other hand, however, owing to its limited stability—due mainly to the fact that it passes through one cortex only, which means that flexural strength is limited—this type of screw is not widely used in external fixation applications.

It would instead be desirable to be able to use an external fixator, which has the advantages of stability and strength typical of provisional fixation systems, and to combine it with the advantages of ease of application, lightness and limited invasiveness that are instead typical of systems that use unicortical pins.

The technical problem forming the basis of the present disclosure is therefore to devise a locking device for unicortical pins to be associated with external fixators, which is able to create a structure sufficiently rigid for it to withstand the external loads acting on it, so as to allow the formation of external fixators that are extremely flexible, but that at the same time have that degree of structural rigidity that typically distinguishes external fixation systems.

The device should have an optimum performance, under traction and compression, of the tip in the cortex of the bone and should eliminate, as far as possible, the flexural stresses acting on the shank of the single screw.

SUMMARY OF THE DISCLOSURE

In some embodiments of the present disclosure, the aforementioned technical problem may be solved by using a locking device for unicortical pins.

In some embodiments of the present disclosure, application of an external fixator to a patient's long bone by means of the unicortical pins is provided for.

The application method described above may make it possible to create fixation systems with exceptional stability, despite its use of unicortical pins only.

Further features and advantages will become clearer from the detailed description provided below of some preferred, but not exclusive, embodiments of the present disclosure, with reference to the attached figures provided by way of non-limiting example.

DETAILED DESCRIPTION

Figure 1:
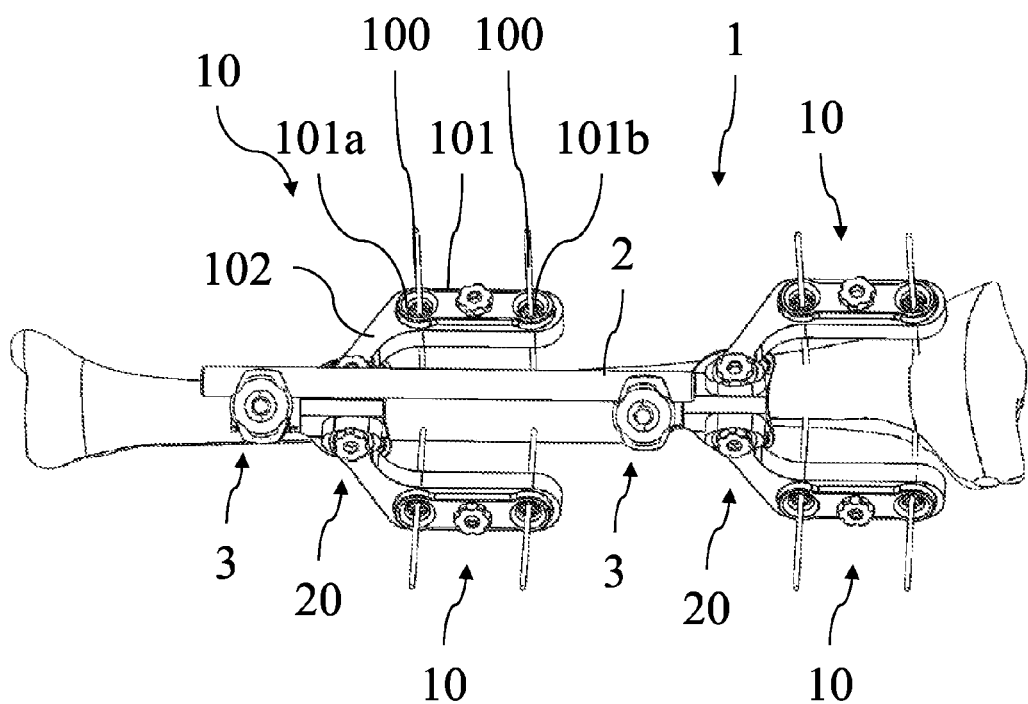
FIGS. 1-4 show different perspective views of an external fixator associated with the long bone of a patient using the method according to the present disclosure, where the locking devices of the distal and proximal anchoring groups are mounted in different configurations.
Figure 2:
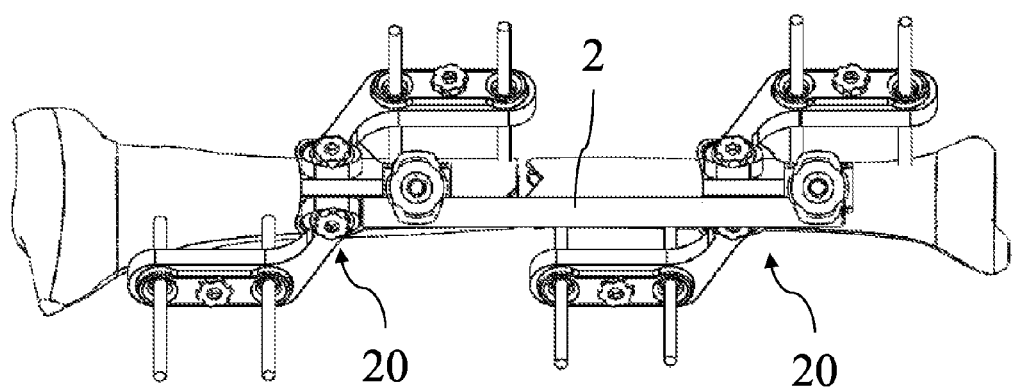
Figure 3:
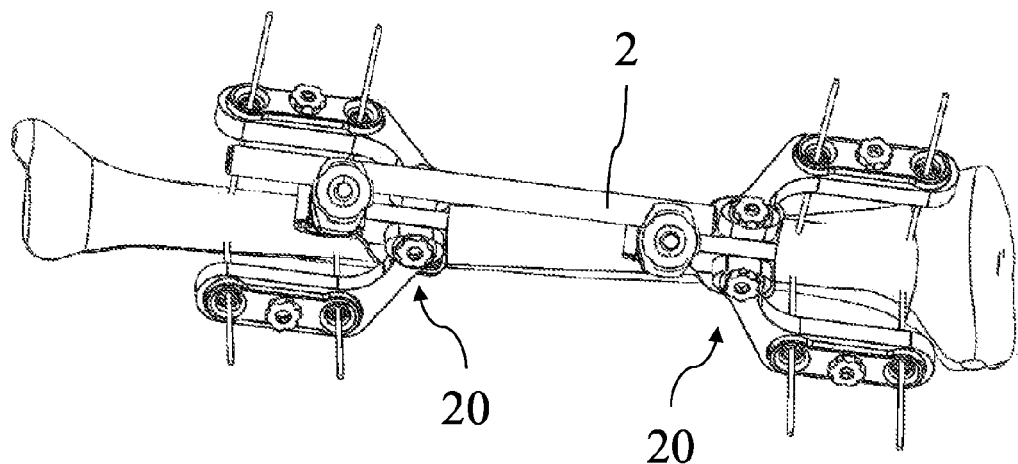
Figure 4:
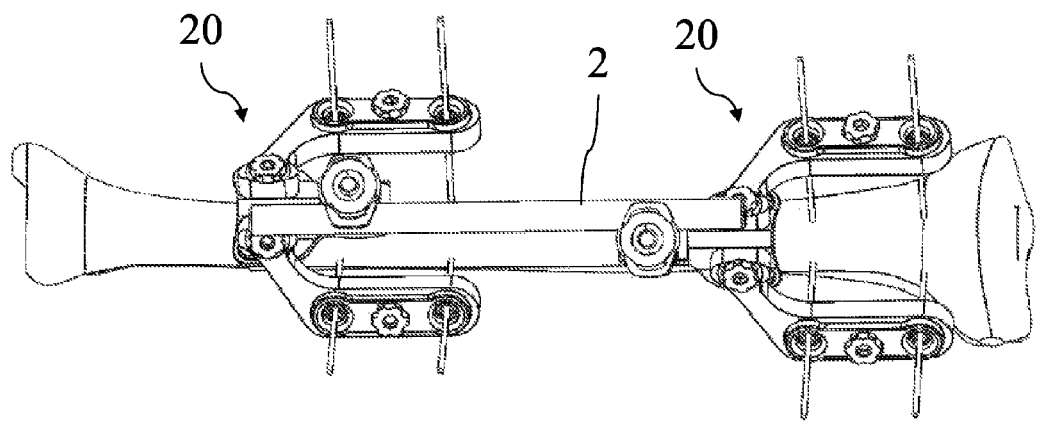
Figure 5:
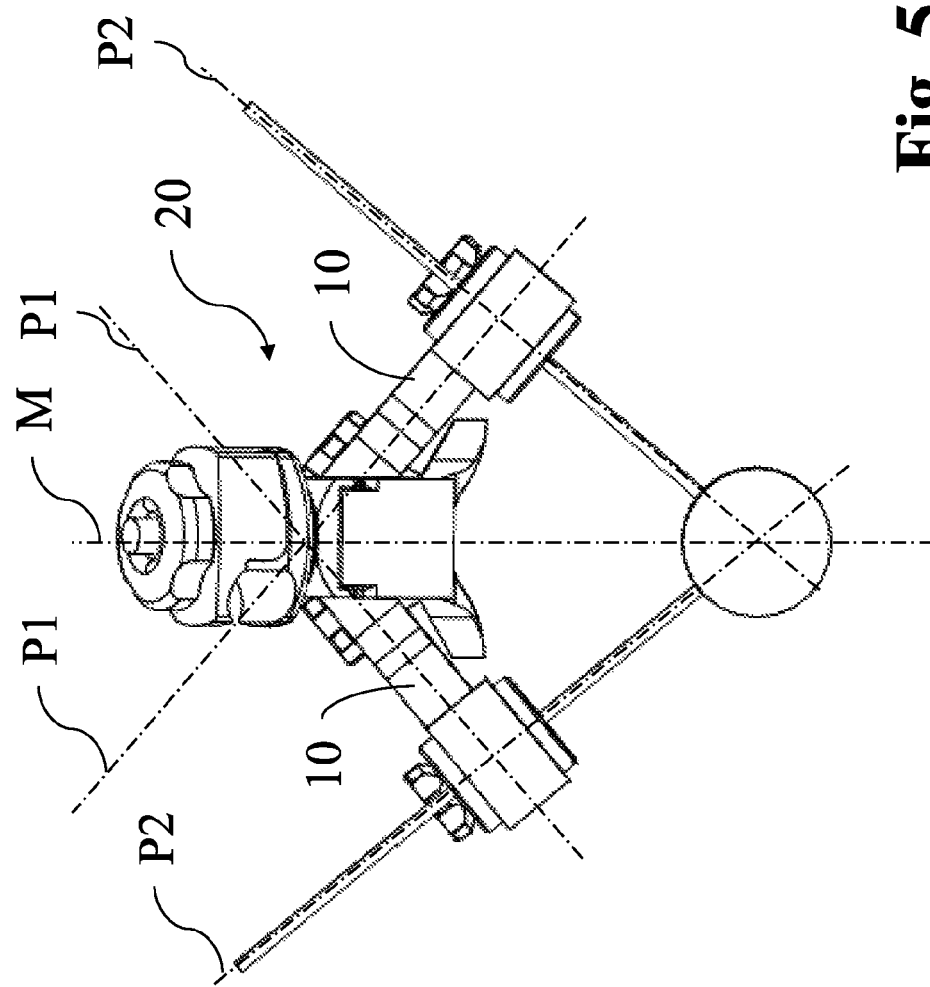
FIG. 5 shows a front view of an anchoring group associated with the bone of a patient.
Figure 6:
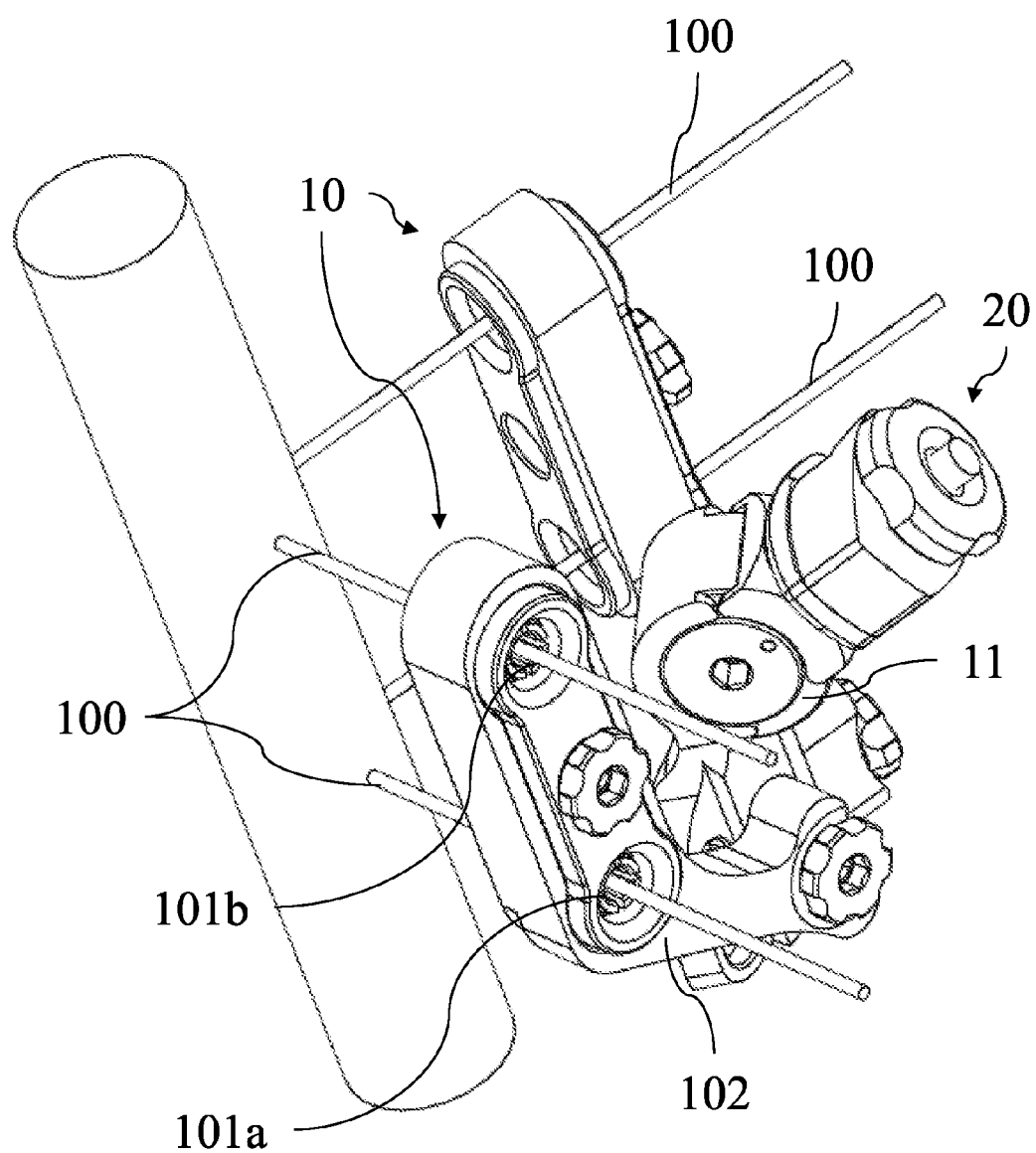
FIG. 6 shows a perspective view of the anchoring group of FIG. 5.
Figure 7:
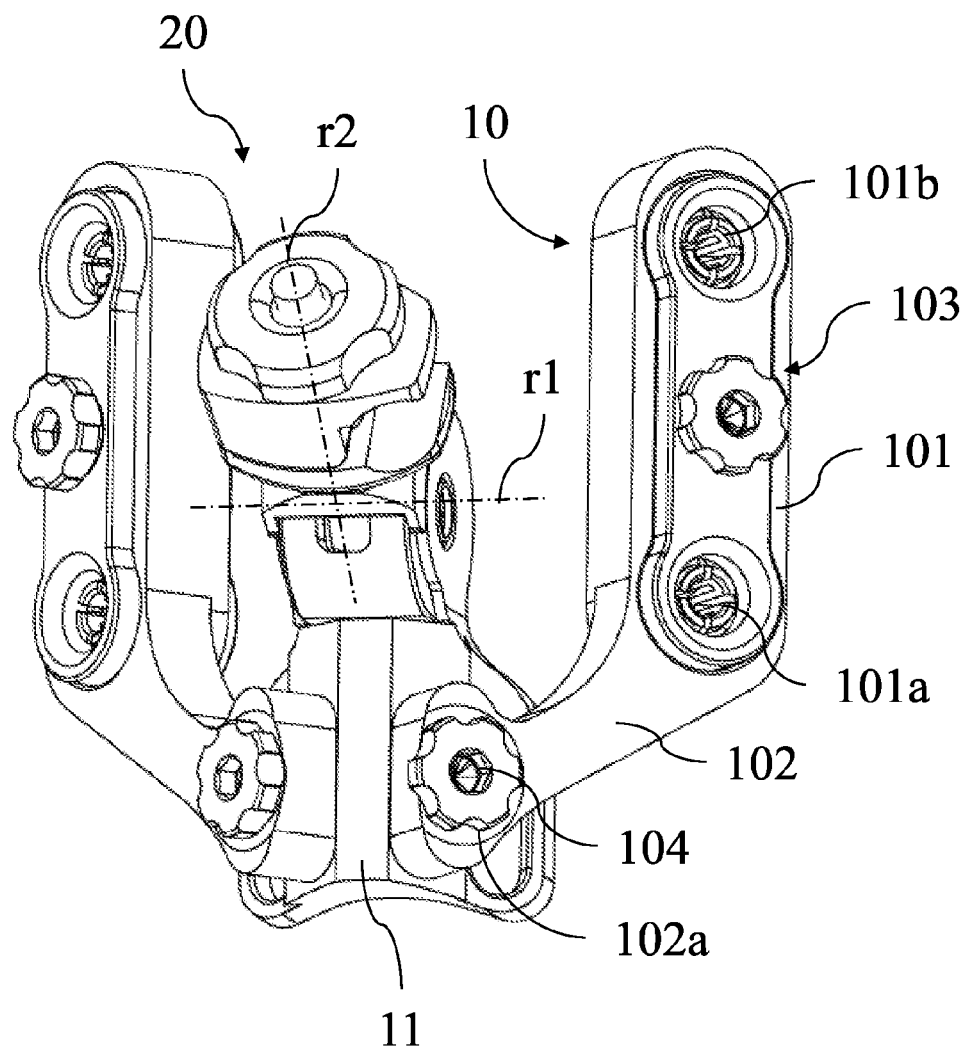
FIG. 7 and FIG. 8 show two perspective views of an anchoring group, in which mounting of the locking devices in two different configurations is shown.
Figure 8:
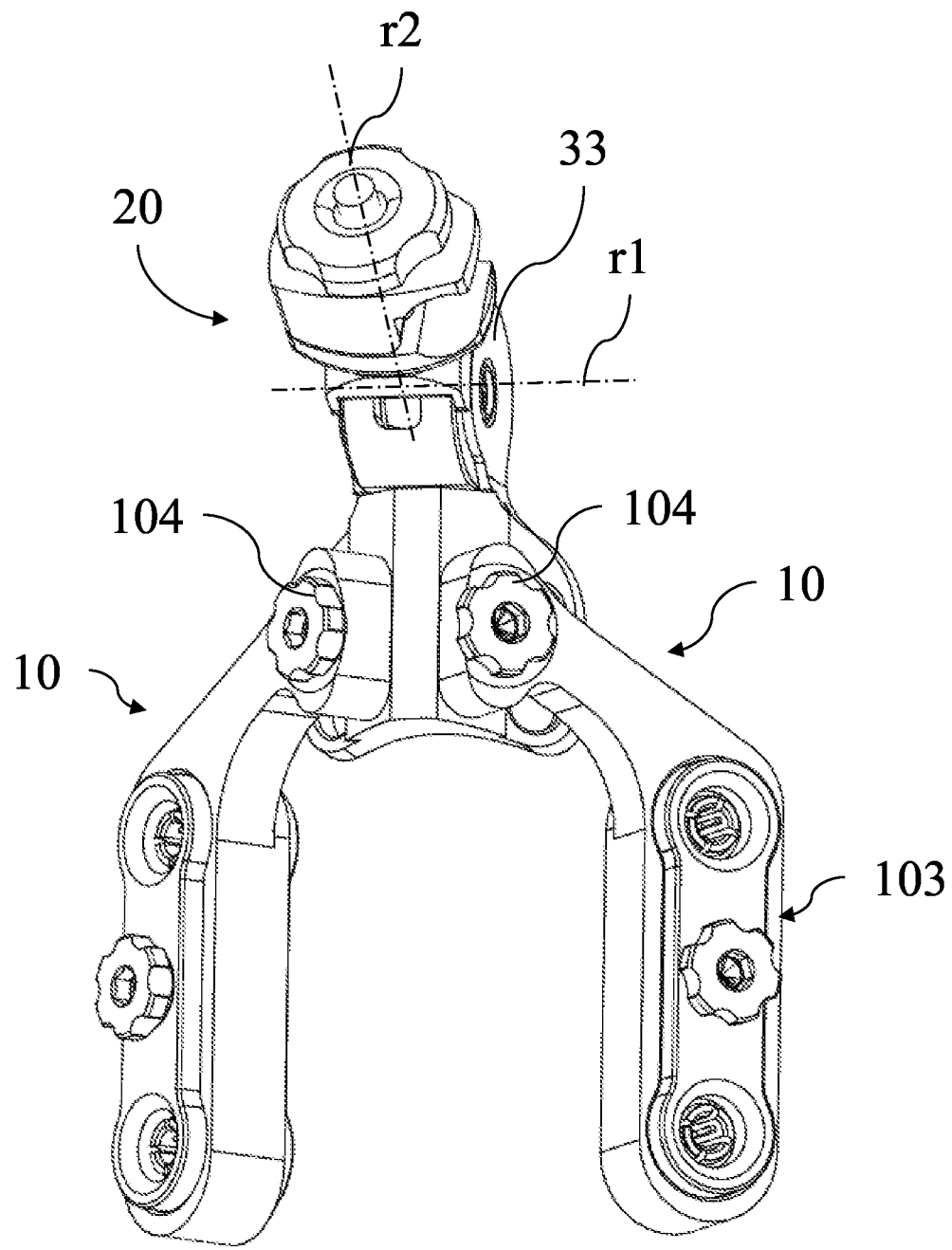
Figure 9:
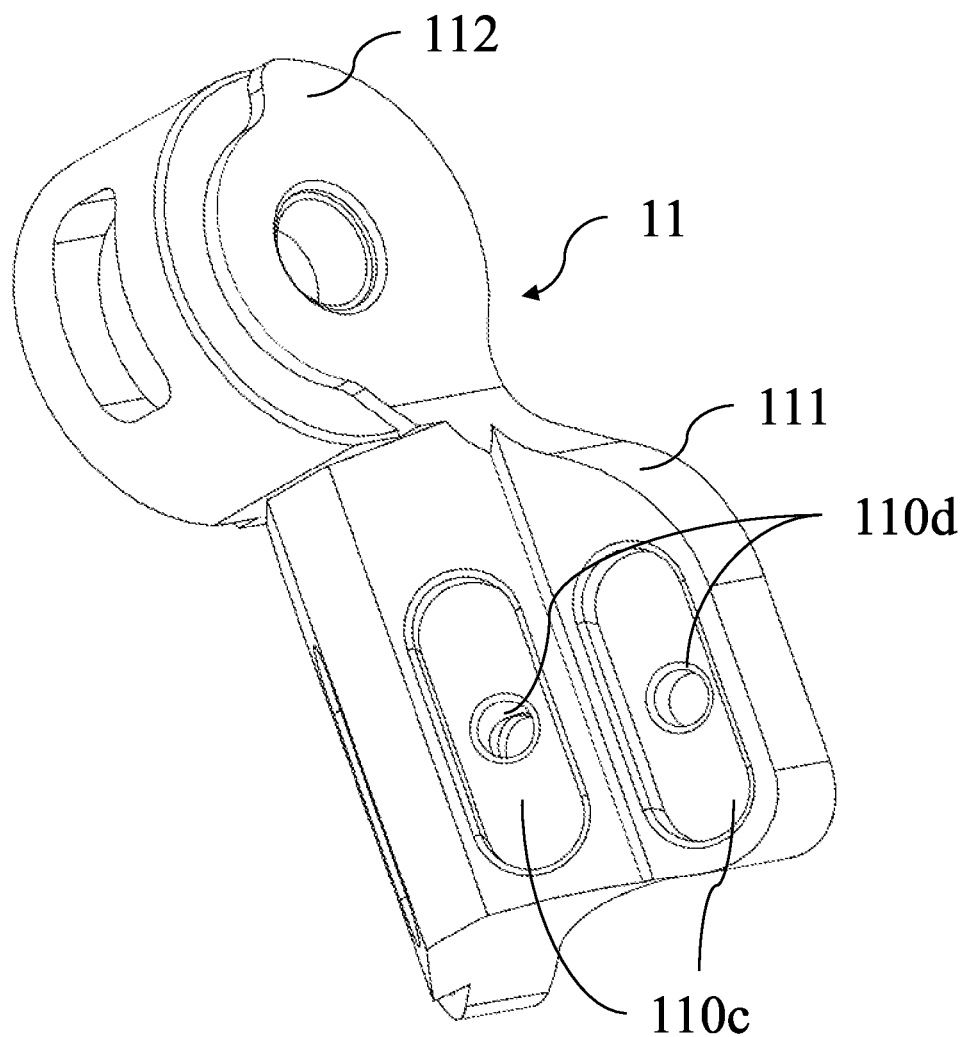
FIG. 9 shows a perspective view of a connecting body of the anchoring group.
Figure 10:
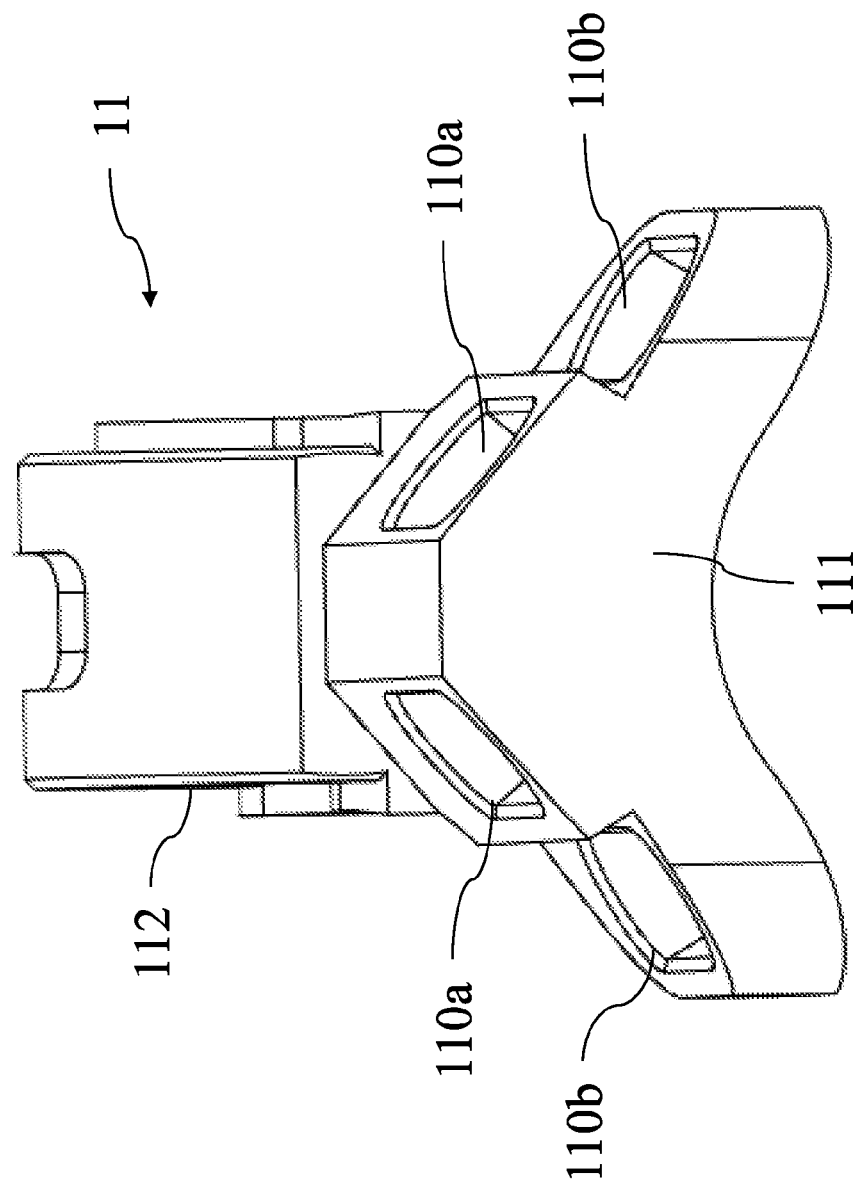
FIG. 10 shows a front view of the connecting body of FIG. 9.
Figure 11:
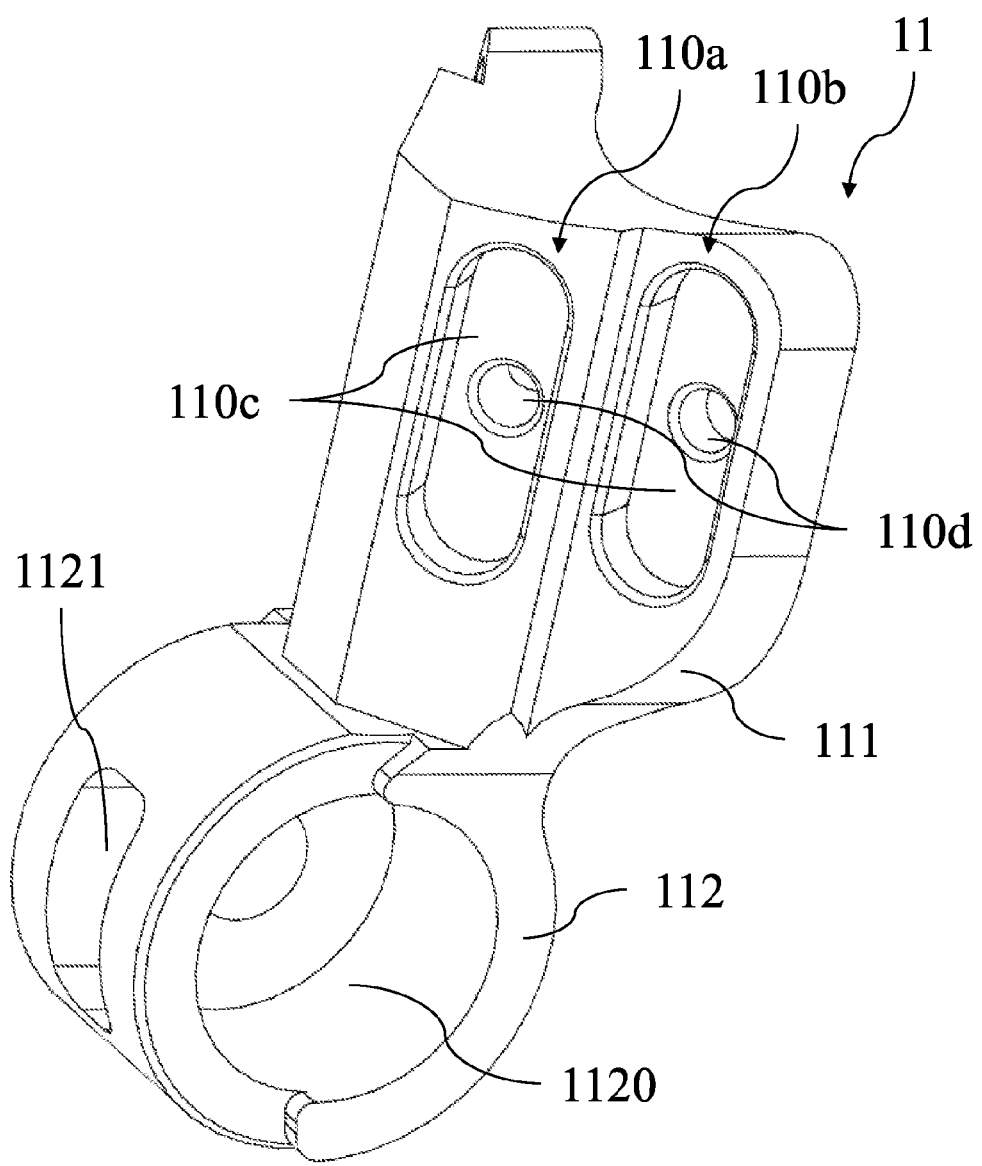
FIG. 11 shows a further perspective view of the connecting body of FIG. 9.
Figure 12:
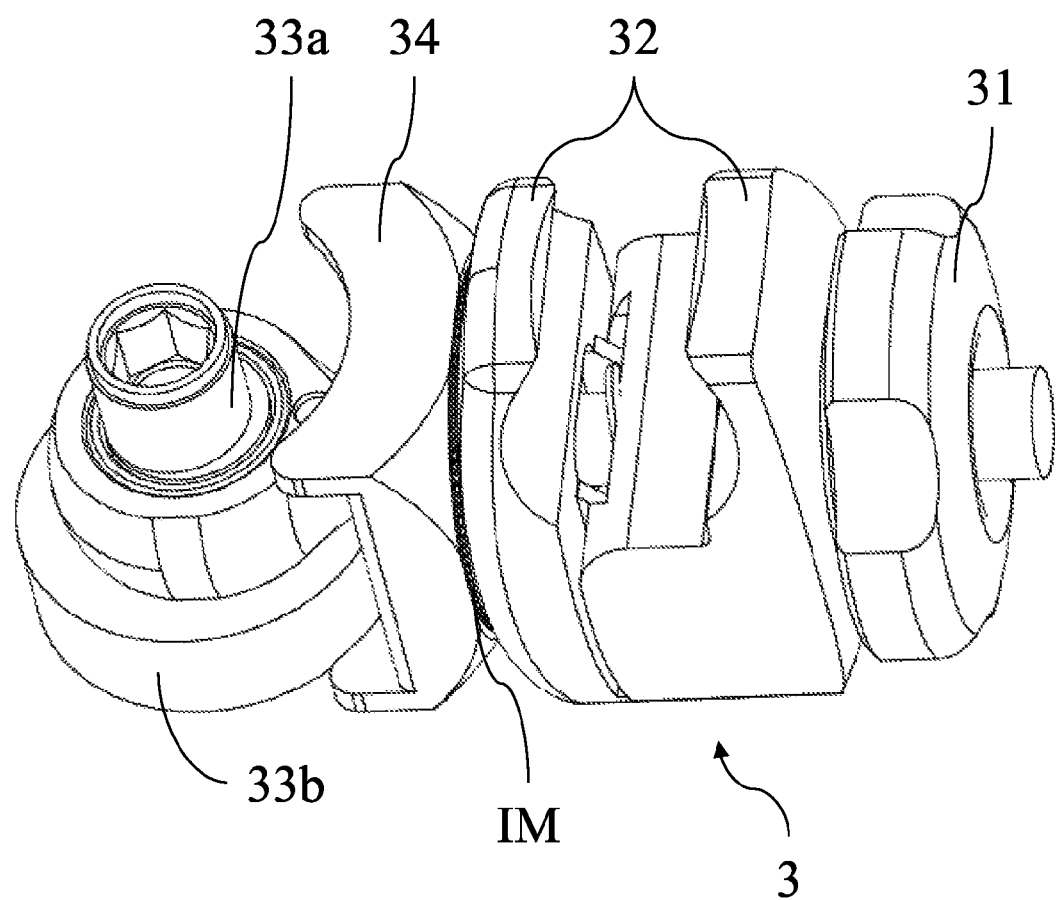
FIG. 12 shows a perspective view of the locking clamp of the anchoring group.

With reference to the attached figures, and in particular to FIGS. 1-4, the reference number 1 denotes overall an external fixator applied according to the method of the present disclosure, to a long bone of a patient using only unicortical pins or screws 100.

The external fixator may comprise in particular a bar 2, known per se, which may be fixed to the bone by means of two anchoring groups 20 which may be respectively arranged in a distal position and proximal position.

Each of the anchoring groups 20 may comprise two locking devices 10, each of which may be designed to be locked into position by two unicortical pins 100 which may be implanted into the bone of a patient. The two locking devices 10 may extend laterally, in the manner of wings, from a central connecting body 11 of the anchoring group which may also support a locking clamp 3 designed to grip the bar of the external fixator 1.

In some embodiments, the locking devices 10 may be made as modular elements which may be mounted separately on the connecting body 11; nevertheless, alternative embodiments may be possible in which the entire anchoring group 20 may be formed as one piece, while retaining the particularly advantageous form and functional characteristics described below.

Figure 13:
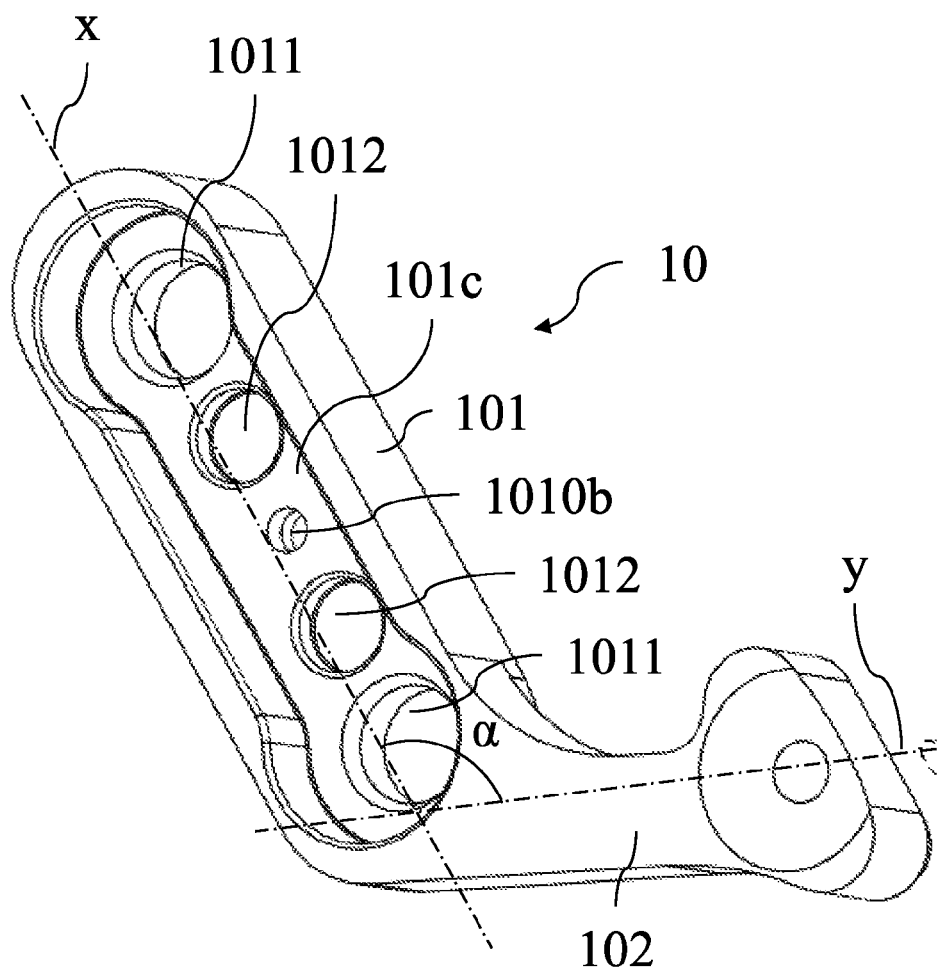
FIG. 13 shows a perspective view of the main body of a locking device.
Figure 14:
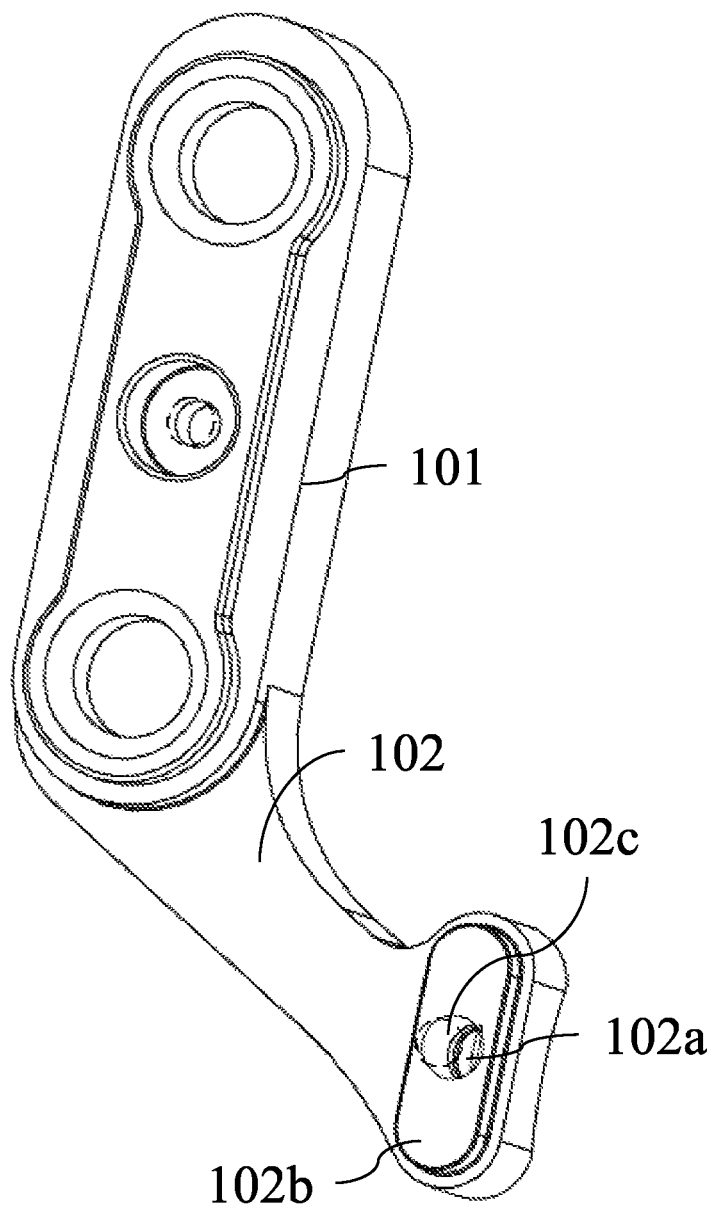
FIG. 14 shows another perspective view of the main body of FIG. 13.
Figure 15:
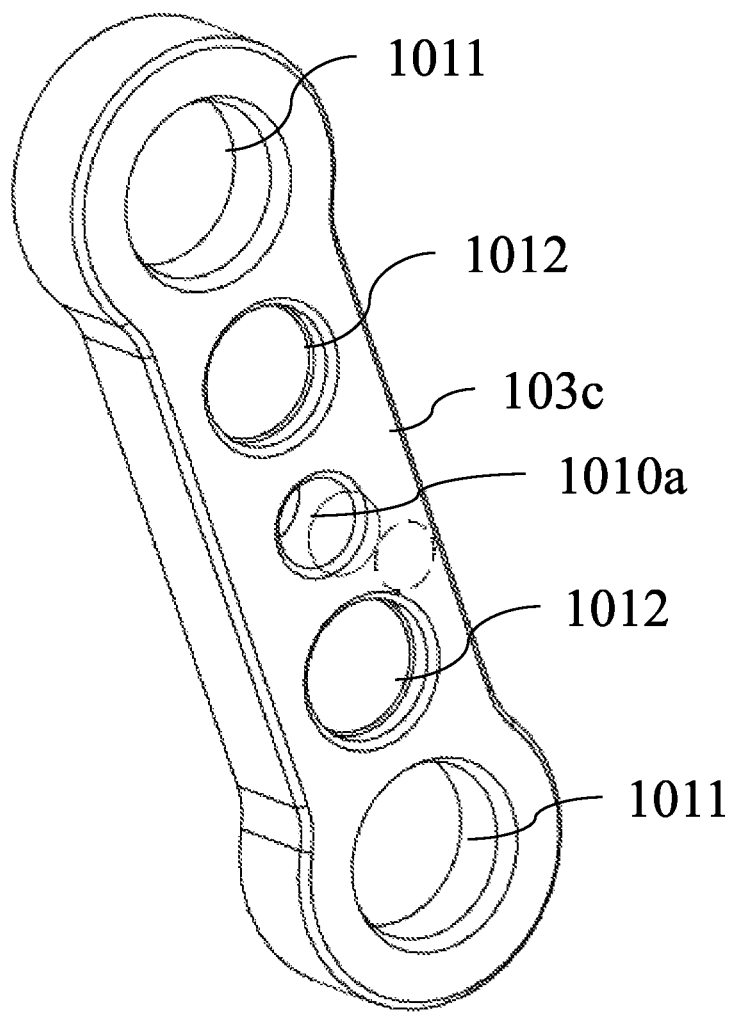
FIG. 15 shows a perspective view of the pressing body of the locking device.
Figure 16:
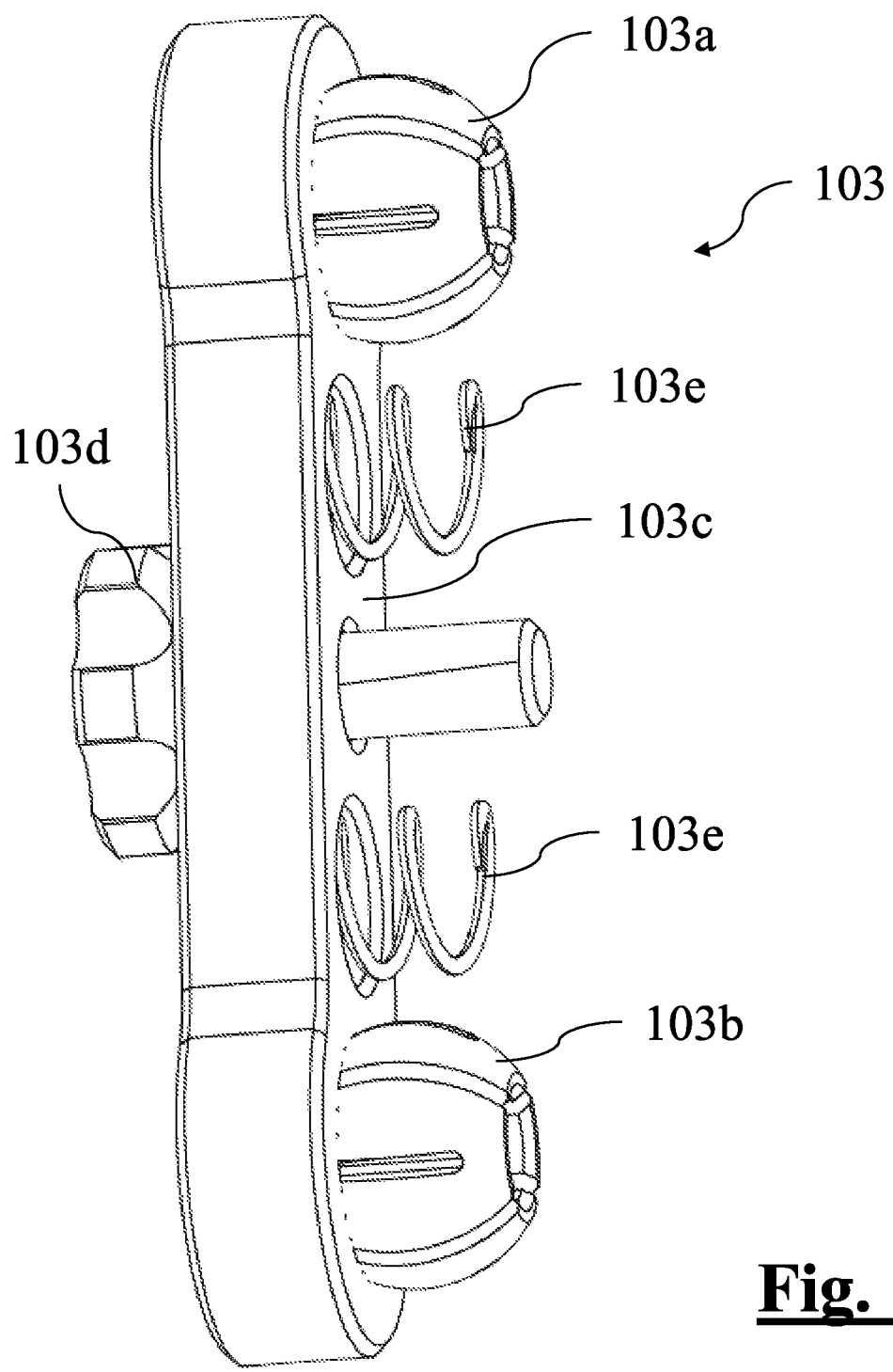
FIG. 16 shows a perspective view of the locking means of the locking device.

The single locking device 10 may have a substantially L-shaped main body. More specifically, the single locking device 10 may have a pin-locking arm 101 and a connection base 102 which may together form an elbow. An angle α between the direction of extension of the arm x and the direction of extension of the base y, shown in FIG. 13, is preferably an angle that is substantially greater than a right angle, namely between 120° and 150°. It may be noted that the pin-locking arm 101 and the connection base 102 may extend along a same plane of orientation $P_1$ of the locking device 10.

The pin-locking arm 101 may have at its two opposite ends two seats 101a, 101b which may be designed to lock a corresponding number of unicortical pins 100. This locking action may be performed by the locking means 103 described below.

Figure 17:
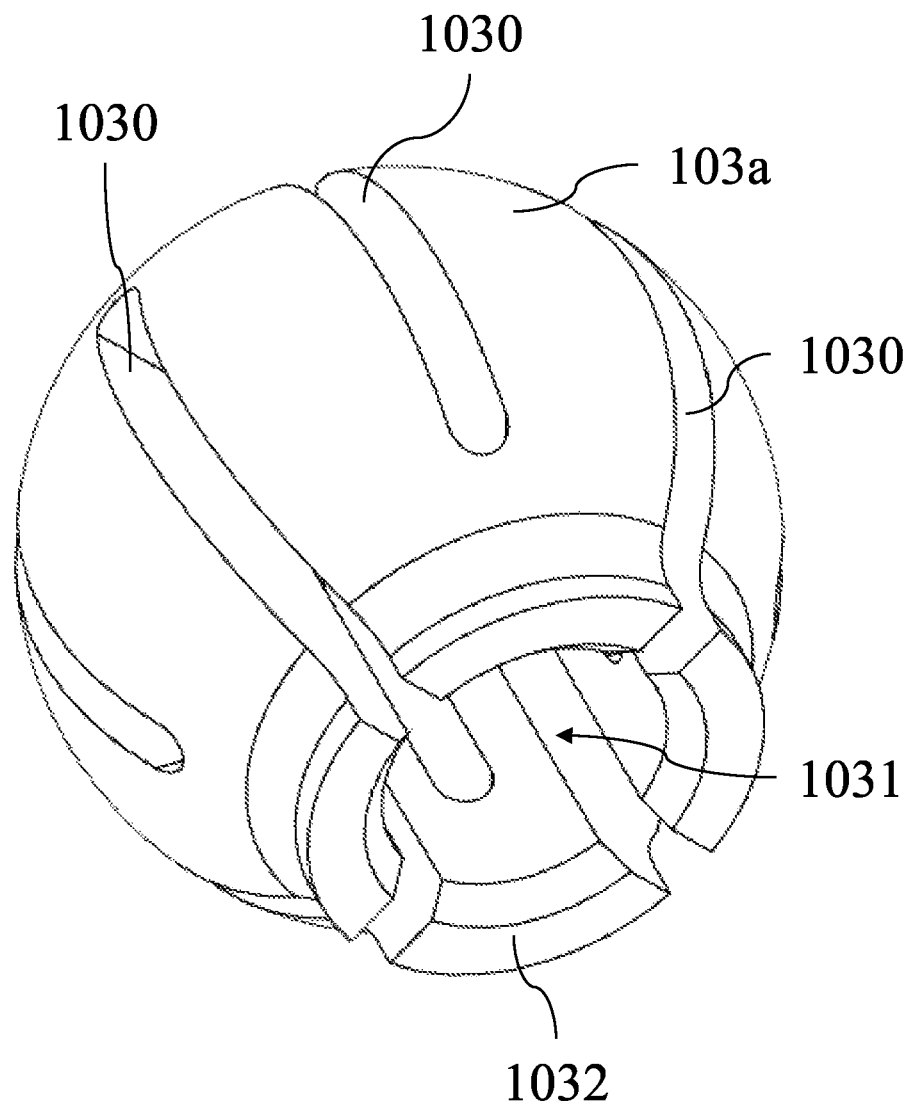
FIG. 17 shows a perspective view of a deformable sphere forming part of the locking means shown in FIG. 16.
Figure 18:
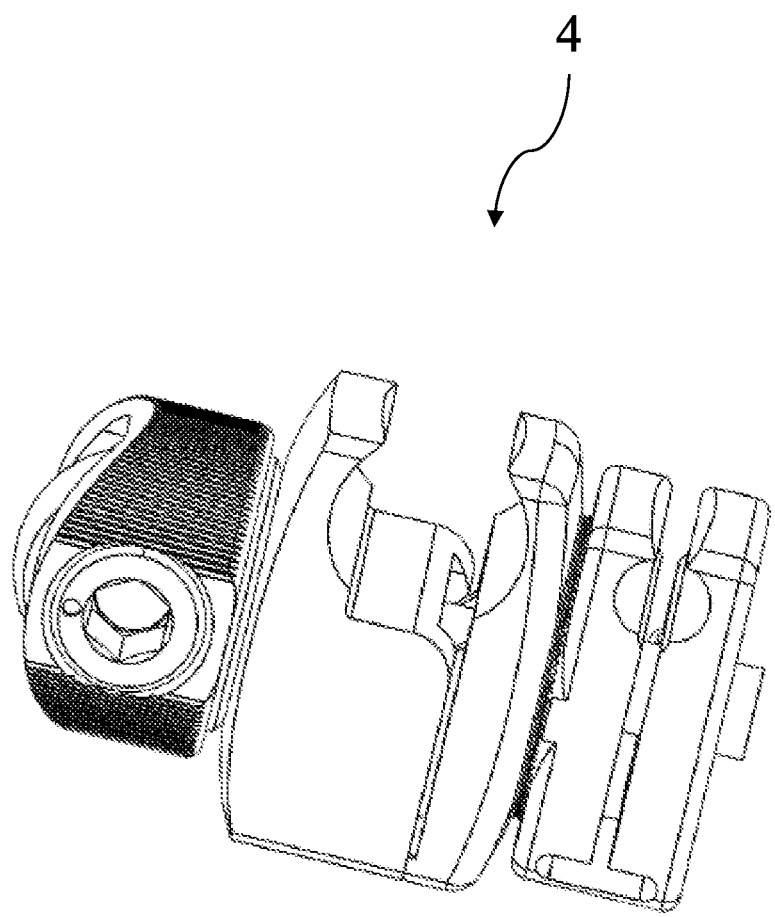
FIG. 18 shows a perspective view of a bar/pin clamp which can be associated with the connection bar of the external fixator.

The locking means 103 may comprise, in particular, two deformable spheres 103a, 103b, one of which is shown separately in FIG. 17, which may be provided with a diametral insertion channel 1031 that defines the actual seat 101a, 101b for the unicortical pins 100. The deformable spheres may have a plurality of incisions that may cross the sphere in a planar manner passing through the insertion channel 1031; the incisions may lead alternately into one or the other of two opposite openings of the insertion channel 1031. Because of the incisions, the sphere may become deformed when it is compressed along the axis of the insertion channel. Thus, the insertion channel 1031 may be constricted locally, by which the unicortical pin 100 housed therein may be locked.

The aforementioned deformable spheres 103 may be housed between an elongated impression 101c, formed along the upper surface of the pin-locking arm 101, and a pressure plate 103a shaped to counter the opposite impression 101c. In particular, both the pressure plate 103c and the impression 101c may have smooth through-holes 1011 at their ends; the two deformable spheres 103 may be locked between two smooth through-holes 1011 situated opposite each other. The insertion channel 1031 of the spheres 103 may be accessible via the smooth through-holes 1011 so as to allow the introduction of the unicortical pin 100.

A pressure plate 103c may be connected to the impression via tightening means 103d which may take the form of a screw. The shank of the screw may be inserted into a central through-hole 1010a of the pressure plate and then into an opposite central hole 1010b formed in the bottom of the impression 101c, on the outside of which it may engage with a nut. Resilient setting means 103e may also be arranged between the pressure plate 103c and the impression 101c, which may be formed in particular by two helical springs that are compressed between the two elements and may be retained inside oppositely arranged depressions 1012 of the impression 101c and the pressure plate 103c.

The springs, which may be arranged in intermediate positions between the deformable spheres 103 and the screw, may oppose the tightening action of the latter. Such arrangement may allow the deformable spheres 103 to be deformed and the unicortical pins 100 to be locked inside them.

It should be noted that when the compression plate is not clamped, the deformable spheres 103 may be rotatable inside their seat, such that the surgeon may modify as required the orientation of the inserted unicortical pins 100. Tightening the head of the screw 103d eliminates this degree of rotational freedom.

The deformable spheres 103 may have, in one of the openings of the insertion channel 1031, a raised cylindrical edge 1032 which, once inserted inside the smooth through-hole 1011, may limit the rotational movement of the element, while may allow access to the insertion channel 1031.

In some embodiments, the deformable spheres 103 may allow the direction of the unicortical pins 100 to be varied with respect to the axis perpendicular to the plane of orientation $P_1$ by about 20°.

The connection base 102 has at its free end a fastening point 102a suitable for connection to the connecting body 11.

Moreover, the connecting body 11 may have, on both sides, two alternative fastening seats 110a, 110b for the connection of the fastening point 102a.

The fastening point 102 of the locking device 10 may present an enlarged portion through which a fastening hole 102c may passes and, on the opposite side of the enlarged portion, a projecting tenon 102b; on the other hand, the fastening seats 110a, 110b may present a depression or mortise 110c shaped to match the tenon 102b, and a fastening hole 110d formed in the bottom of the mortise 110c.

When the tenon 102b is correctly inserted into the mortise 110c of one of the fastening seats 110a, 110b, the two fastening holes 102c, 110d may be aligned so that a threaded connection element 104 that fixes the locking device 10 to the connecting body 11 may pass through them.

The connecting body 11 may have a structure that is substantially symmetrical with respect to its median plane M. Said connecting body 11 may have a cusp portion 111 at the front with opposite inclined surfaces that are symmetrical with respect to said median plane M, and at the rear a hinge portion 112, which will be described below.

Both the inclined surfaces of the cusp portion 111 have a top section with an inclination greater than the horizontal and a bottom section with a smaller inclination. The first fastening seat 110a may be formed on the first section and the second fastening seat 110b may be formed on the second section. Thus, depending on whether the locking device 10 may be connected to the first fastening seat 110a or to the second fastening seat 110b, two different inclinations of the plane of orientation $P_1$ with respect to the median-plane M may be obtained. Consequently, also the inclination of the preferential plane of orientation $P_2$ of the unicortical pins 100 may be modified, i.e. the plane on which the pins lie, with due allowance for any adjustments performed by means of the deformable spheres 103a, 103b.

The inclination imparted to the fastening seats 110a, 110b in the present disclsoure may be such that, by associating both locking devices 10 with the respective first seat 110a, an angle between the two planes of orientation $P_1$ may be created that is smaller than a right angle; on the other hand, by associating the locking devices 10 with the second seat 110b, an angle between the two planes of orientation $P_1$ may be obtained that is greater than a right angle. The first configuration may be particularly suitable for small-size bones (e.g., tibial mounting), while the second configuration may be suitable for large-size limbs (e.g., femoral mounting).

The hinge portion 112 of the connecting body 11 may allow for articulation, around an axis of rotation $r_1$ perpendicular to the median plane M, of a locking clamp 3.

The hinge portion 112 may define in particular a cylindrical seat 1120 intended to define interiorly an articulation hinge 33 of the locking clamp 3. A threaded element, with a shank which defines the pin 33a of the hinge 33 and a head which acts as a cover for the cylindrical seat 1120, is in fact screwed laterally into the cylindrical seat 1120. A shank 30 of the locking clamp 3, which may comprise an eyelet end 30a, which may embrace the aforementioned pin 33a, may also be inserted, via an upper groove 1121, inside the cylindrical seat 1120.

Outside of the cylindrical seat, the shank 30 may pass through, in succession, an intermediate element 34, slidably movable along an outer cylindrical surface of the hinge portion 112, and two jaws 32 designed to grip in a known manner the bar 2 of the external fixator. A splined coupling IM may be formed between the bottom jaw 32 and the intermediate element 34 that ensures restriction of rotation when the two parts are clamped against each other. The free end of the shank 30 may be threaded and a lock nut 31 may be screwed onto it.

When the abovementioned group is not clamped, adjustments both around the axis of rotation $r_1$ of the hinge and around the axis $r_2$ of the shank 30 may be possible. Tightening the lock nut 31 may cause the entire group to be pressed together and performs the triple function of locking the bar 2 between the jaws of the clamp 3 and blocking the two abovementioned rotational axes. In particular, the axis of rotation $r_1$ may be blocked by the friction between the intermediate element 34 and the outer cylindrical surface of the hinge portion 112, and the axis of rotation $r_2$ may be blocked by the locking action of the splined coupling IM.

Having described individually the single elements which make up the anchoring groups 20 of the external fixator 1, description is now provided below for the different possibilities of assembling them in order to obtain different configurations of the said fixator.

First of all, the locking devices 10 may be constructed in two configurations which may be a mirror image of each other, namely a configuration oriented to the right of the connection base 102 and a configuration oriented to the left of the connection base 102.

The external fixator 1, which by nature is modular, may comprise both right-hand and left-hand locking devices 10 which may be used alternatively by the surgeon in the field depending on the actual operating requirements.

Thus, depending on the locking devices chosen, each anchoring group 20 may be mounted in three different configurations: a U configuration, in which the two locking devices 10 may both be oriented in the same direction, away from the locking clamp 3 of the anchoring group 20; an M configuration, in which the two locking devices 10 may both be oriented in the direction of the locking clamp 3 of the anchoring group 20; and an S configuration, in which the locking devices 10 are oriented in opposite directions.

With reference to the enclosed figures: FIG. 1 shows an external fixator 1 in which both anchoring groups 20 have a U configuration; in FIG. 2 both anchoring groups 20 have an S configuration; in FIGS. 3 and 4 the proximal mounting group 20 has a U configuration and the distal group has an M configuration, i.e. in a position where the pin-locking arms 101 point in a distal direction and proximal direction, respectively.

The various configurations described above may be used alternatively by the surgeon, depending on the specific operating requirements and the morphology of the fractured bone. In particular, with the S configuration two unicortical pins 100 may be arranged in the vicinity of the fracture site, thereby increasing stability. It is a known fact that the relative spacing of the screws may improve the stability of an external fixator 1.

In the case where additional stability is required, further unicortical pins 100 may be added, being directly fixed to the bar 2 by means of one or more bar/pin clamps 4 of the type known in the art.

In some embodiments, methods for applying an external fixator 1 are provided. Methods may comprise the following steps:

preparing the first anchoring group 20, for example the distal anchoring group of the type described above, where necessary mounting it in the configuration most suitable for the intervention according to the modes described above;

inserting unicortical pins 100 in at least three of the seats 101a, 101b (but preferably all four of them) of the two pin-locking devices 101 of the anchoring group 20;

fixing the unicortical pins 100 to the long bone of the patient, rotating them by means of a special instrument, using the seats 101a, 101b as boring guides;

locking said unicortical pins 100 inside the seats 101a, 101b using the special locking means 103 described above.

It should be noted that before fixing the unicortical pins 100 to the bone, they may be oriented by rotating the deformable sphere 103a, 103b in which they are inserted and then locking them in position by tightening the aforementioned locking means 103.

It should in particular be noted that the unicortical pins may have a self-tapping tip so that it may be sufficient to rotate them, associating their head with a drilling device in order to create the fixation hole in the patient's bone, whereby said hole may only penetrate the first cortex.

The steps described above may then be repeated in order to fix a second anchoring group 20, for example the proximal anchoring group; following which, by performing the adjustments along the axes $r_1$ and $r_2$ of the locking clamps 3 of the two anchoring groups 20, they are aligned and connected to the bar 2.

As previously mentioned, in order to improve the stability of the external fixator, further unicortical pins 100, preferably two in number, may be used, associating them directly to the bar 2 by means of bar/pin clamps 4.

It should be noted that, during mounting of the anchoring groups, owing to the L-shaped form of the locking device 10, X-ray access to the bone site concerned in the intervention is never obstructed by the structure of the anchoring groups, so that the various parts which make up the group need not necessarily be made of radiotransparent material.

It should also be noted that the non-invasive form of the anchoring group 20, in particular in its U configuration with the opening directed towards the bone end, may allow for easy access of an instrument for reaming the long bone of the patient and subsequently inserting an intramedullary nail, even when the anchoring group is positioned at the point where the nail end is inserted.

One of ordinary skill in the art, in order to satisfy specific requirements which may arise, may make numerous modifications and variations to the devices described above, all of which are however contained within the scope of protection of the disclosure, as defined by the following claims.

The invention claimed is:

1. A method for surgical application of an external fixator to a long bone of a patient, the method comprising:
providing a first anchoring group, wherein the first anchoring group comprises a connecting body associated with a bar locking clamp and two locking devices, both locking devices comprising: a pin-locking arm provided with two seats suitable for locking a corresponding number of unicortical pins; and a connection base which extends in an angled relationship with respect to the pin-locking arm and away from both seats, the connection base being coupled to the connecting body at a fastening point that is not aligned with said seats, the pin-locking devices extending respectively from either side with respect to a median plane (M) of the connecting body;
inserting unicortical pins in at least three seats of the two pin-locking arms;
affixing the unicortical pins to the long bone of the patient, rotating them, using the seats as boring guides, until a self-tapping tip of the unicortical pins is inserted into a cortex of the patient's bone, so that the unicortical pins are screwed to a single bone cortex only and do not reach the medullary cavity of the bone;
locking the unicortical pins when passing through one cortex only inside the seats for locking the pin-locking arms;
further comprising adjusting an orientation of the unicortical pins with respect to the long bone of the patient by rotating deformable spheres inside of which a diametral channel is formed that defines the seats of the pin locking devices, wherein locking the unicortical pins inside the seats further comprises compressing the deformable spheres by means of a tightening screw and a pressure plate that can be tightened when needed, against the pin-locking arm; and
wherein each of the pin-locking arms further comprises at least one helical spring positioned between the pressure plate and the pin-locking arm to oppose the tightening of the pressure plate against the pin locking arm, thereby providing the deformable spheres with rotational freedom when the tightening screw is loosened.

2. The method according to claim 1, further comprising providing a second anchoring group, affixing the second anchoring group to the long bone by means of at least three unicortical pins, connecting the first and the second anchoring group by means of a bar connected to the locking clamps of said groups.

3. The method according to claim 2, further comprising affixing the bar to the long bone by means of at least one additional unicortical pin, connected to the bar by means of a bar/pin clamp.

4. The method according to claim 1, wherein the two locking devices are removably associated with at least one fastening seat of the connecting body, the step of providing the first anchoring group comprising a step of mounting the two locking devices on the connecting body.

5. The method according to claim 4, wherein the connecting body has at least two fastening seats for each locking device so as to allow at least two alternative mounting configurations, a mounting of the locking device on either one of the fastening seats of the connecting body defining different inclinations of a plane of orientation ($P_1$) of the locking device with respect to a median plane (M) of the connecting body, the method comprising a step of selecting the fastening seats with which the locking devices are to be associated depending on dimensions of the long bone onto which the first anchoring group is to be applied.

6. The method according to claim 4, wherein the locking devices may have two alternative configurations that are a mirror image of each other, the alternative mounting of the locking devices on opposite sides of the connecting body allowing for formation of a plurality of alternative configurations of the anchoring group, the method comprising a step of selecting an optimum configuration for a type of operation to be performed.

7. The method according to claim 6, wherein in the mounting step the first anchoring group is arranged in an S configuration in which the two locking devices have their respective pin-locking arms oriented in opposite directions.

8. The method according to claim 6, wherein in the mounting step the first anchoring group is arranged in an M configuration in which the two locking devices have their respective pin-locking arms both oriented in the direction of a locking clamp associated with the connecting body.

9. The method according to claim 6, wherein in the mounting step the first anchoring group is arranged in a U configuration in which the two locking devices have their respective pin-locking arms both oriented in the direction opposite a locking clamp associated with the connecting body.

10. The method according to claim 1, wherein the connecting body has a first pair of fastening seats and a second pair of fastening seats, a mounting of both locking devices to the first pair of fastening seats of the connecting body defining two first planes of orientation (P1) with an angle smaller than a right angle, while a mounting of both locking devices to the second pair of fastening seats of the connecting body defining two second planes of orientation (P2) with an angle greater than a right angle.

* * * * *